United States Patent [19]

Yamada et al.

[11] 4,344,904

[45] Aug. 17, 1982

[54] SINTERING METHOD OF ZIRCONIA

[75] Inventors: Koichi Yamada; Yasuo Shinya, both of Niihama, Japan

[73] Assignee: Sumitomo Aluminium Smelting Co., Ltd., Osaka, Japan

[21] Appl. No.: 190,845

[22] Filed: Sep. 25, 1980

[30] Foreign Application Priority Data

Sep. 28, 1979 [JP] Japan ................. 54/125589

[51] Int. Cl.³ ............................. C04B 35/48
[52] U.S. Cl. ...................... 264/66; 264/235; 264/346; 501/103; 501/104
[58] Field of Search .................. 264/66, 235, 346; 106/57; 501/103, 104

[56] References Cited

U.S. PATENT DOCUMENTS 3,175,919 3/1965 Smoot ............................. 106/57
4,205,051 5/1980 Tokahashi ....................... 106/57

FOREIGN PATENT DOCUMENTS 53-128612 11/1978 Japan .

*Primary Examiner*—John A. Parrish
*Attorney, Agent, or Firm*—Wenderoth, Lind & Ponack

[57] ABSTRACT

A method is provided for producing a sintered zirconia article excellent in thermal shock resistance and high in sintered density. The method comprises mixing zirconia powder as the starting material and a stabilizing agent with a definite amount of partially stabilized zirconia powder, shaping and sintering the mixture, and heat treating it under specific temperature conditions.

7 Claims, No Drawings

SINTERING METHOD OF ZIRCONIA

The present invention relates to a method of producing a sintered zirconia article excellent in thermal shock resistance and high in sintered density, and more particularly to a method of producing a sintered zirconia article having excellent thermal shock resistance and high sintered density by mixing zirconia powder as the starting material and a stabilizing agent with a definite amount of partially stabilized zirconia powder, shaping and sintering the mixture, and heat-treating it under a specified temperature condition.

In the case of sintering zirconia powder alone as the starting material, there arises in the vicinity of 1000° C., a phase transition from a monoclinic phase to a tetragonal phase, accompanied by a great volume change, and in the course of temperature elevation and cooling, the sintered article becomes broken. Therefore, in conventional methods of producing a sintered zirconia article, one or more stabilizing agents such as CaO, MgO, $Y_2O_3$, etc. are added to zirconia to make said stabilizing agent form a solid solution with zirconia so that a sintered zirconia article having a cubic phase is formed, thereby preventing breakage.

Among the sintered articles thus obtained, zirconia composed singly of cubic crystal structures is called fully stabilized zirconia, and is supplied for refractory elements, oxygen sensors, etc. as a solid electrolyte. However, the fully stabilized sintered zirconia article has a relatively large thermal expansion coefficient, and therefore in an atmosphere accompanied by a rapid temperature change, such as in exhaust gas from an internal-combustion engine, an excessive thermal stress is generated in the interior of the sintered article, so that such a zirconia article cannot be used. Accordingly, there have been studied various methods of improving the thermal shock resistance of the fully stabilized sintered zirconia article. For example, a sintered zirconia article for use as an oxygen sensor has been proposed which is produced by maintaining 5–35 weight % of monoclinic crystal structures present in a sintered zirconia and which is subjected to a stabilizing treatment to convert it into a cubic crystal structure (laid-open Japanese Patent Application No. 128612/1978).

In the case of the above mentioned sintered article, the monoclinic structures present in the sintered article give rise to a crystal transformation (phase transition) from a monoclinic to a tetragonal structure and from a tetragonal to a monoclinic structure during the use of said sintered article, and a volume change arises in the monoclinic crystal portions which will then scatter to form gaps in said crystal structure portions. This sintered article is improved in its thermal shock resistance by utilizing this phenomenon to absorb the thermal stress generated in the cubic portions. Although this sintered article is improved in thermal shock resistance in comparison with the fully stabilized zirconia article, it does not always afford satisfactory results to applications in a severe condition, such as use as sensors for the measurement of the oxygen concentration in molten iron. Therefore, it is now desired to produce a sintered zirconia article which has higher thermal shock resistance.

Under these circumstances, the present inventors have extensively studied to find a method of producing a sintered zirconia article excellent in thermal shock resistance and having a high sintered density, as required for such uses as oxygen sensors. As a result, it has been found that a sintered zirconia article satisfying all the above mentioned requirements can be obtained by mixing zirconia powder as the starting material and a stabilizng agent with a definite amount of partially stabilized zirconia powder, shaping and sintering the mixture and heat-treating it under specified temperature conditions to form a sintered article composed of specific crystal structures and made up of a composition in the form of particles.

In accordance with the present invention, there is provided a method of producing a sintered zirconia article, characterized by mixing 10–50% by weight of a partially stabilized zirconia powder obtained by adding a stabilizing agent to a zirconia powder, sintering the admixture and pulverizing the sintered admixture, with 90–50% by weight of a zirconia powder and a stabilizing agent, shaping the resulting mixture, sintering the shaped article and then heat treating the sintered article at a temperature of from 1200° to 1500° C., thereby to obtain a sintered zirconia article composed of cubic phase crystal of not more than 70% by weight in crystal structures and constituted of 5–40% by weight of particles in a diameter of 1–30μ and 95–60% by weight of particles in a diameter of 30–200μ.

The present invention will be explained in detail hereunder.

In the present invention, the starting materials are a zirconia powder, a stabilizing agent and a partially stabilized zirconia powder. The partially stabilized zirconia powder is obtained by admixing a zirconia powder with a stabilizing agent, sintering the admixture and pulverizing the sintered admixture, and has partially monoclinic crystal structure in the sintered admixture. These starting materials are thoroughly mixed and shaped. Regarding a stabilizing agent added to and mixed with the zirconia powder, any known stabilizing agent for obtaining a stabilized sintered zirconia article may be properly used. Thus, CaO, MgO, $Y_2O_3$ and the like are exemplified. In the present invention, one or more of said stabilizing agents may be mixed with a zirconia powder and the amount of addition is not more than 15 mol %, preferably within the range of from 3 to 10 mol %. This ratio is the same as the mixing ratio used in preparing the partially stabilized zirconia powder.

As regards the particle size of the starting material zirconia powder, stabilizing agents and partially stabilized zirconia powder, there is no particular limitation, but usually particles having a diameter not larger than 20μ, preferably not larger than 10μ are used.

The mixing ratio of the starting materials is 10–50% by weight of partially stabilized zirconia powder and the remainder, is, 90–50% by weight of the zirconia powder and stabilizing agent.

If the amount of partially stabilized zirconia powder exceeds 50% by weight, it is impossible to obtain a sintered article having a high sintered density (for example 5.4 g/cm$^3$ or higher) required for desired use such as oxygen sensors. On the other hand, if the amount is less than 10% by weight, the ratio of coarse particles in a sintered article increases, and therefore it is impossible to obtain a sintered article having the specified particle size composition, so that an improvement in thermal shock resistance cannot be attained. Also, when partially stabilized zirconia powder is not used, it is impossible to obtain a sintered zirconia article having a high sintered density, even if the sintered zirconia article is produced so that the particle size composition after sintering and then heat-treating takes the specified particle size composition in the present invention by compounding particle sizes (for example, by compounding previously the starting zirconia powder and stabilizing agent so that particles having 1–30μ in diameter constitute 5–40 weight % and particles having 30–200μ in diameter constitute 95–60 weight %, and sintering and then heat-treating the mixture).

In the present invention, the mixture of the partially stabilized zirconia powder, the zirconia powder and the stabilizing agent prepared by mixing in the ratio mentioned above, is then shaped and sintered by a known method, and further heat-treated at a temperature of from 1200° to 1500° C.

In this way, a sintered zirconia article is obtained whose crystal structure after the heat-treatment is composed of a cubic phase structure of not more than 70% by weight, preferably 10–50% by weight in crystalline structure and whose particle distribution is made up of 5–40% by weight of particles in a diameter of 1–30μ and the remainder is 95–60% by weight of particles having a diameter of 30–200μ.

If the cubic crystal structure formed in said sintered article exceeds 70% by weight, the thermal expansion coefficient of the thus obtained sintered article increases and no improvement in thermal shock resistance is observed, so that such an amount is not suitable.

Also, in the case where particles having diameters of 1–30μ and a sintered crystal structure of less than 5% by weight, and in the case where particles having diameters 30–200μ exceeding 95% by weight, the thermal shock resistance is low. On the other hand, if particles having 1–30μ in diameter exceed 40% by weight and particles having 30–200μ in diameter are less than 60% by weight, it is impossible to obtain a sintered article having a high sintered density required for use as oxygen sensors.

In order to obtain a sintered article having such desired physical properties, it is necessary to control such factors as the mixing ratio of the starting material zirconia powder, the sintering conditions, the heat treatment conditions, etc. As regards the sintering conditions, the starting material mixture, shaped to a desired form, is sintered at a temperature of from 1500° to 1900° C., preferably from 1600° to 1800° C. for a period of 0.5 to 30 hours, preferably 1 to 15 hours. As for the condition of the subsequent heat treatment, the sintered article is annealed at a temperature of from 1200° to 1500° C., preferably from 1250° to 1350° C. for a period of 1 to 30 hours, preferably 5 to 20 hours. If the heat treatment of the present invention is not carried out, the improving effect on the thermal shock resistance is extremely low, even if the other conditions are controlled so that they fall within the same condition range as specified in the present invention.

As regards the starting material used in the present invention, only zirconia powder and stabilizing agents were mentioned. However, they are the main or essential components, and of course it is possible to use an accelerating agent for sintering and a promoting agent for particle growth known in the fields concerned, such as silica, alumina, titania, kaolin, mullite, etc., in an amount within the range in which the effects of the present invention are not impaired.

In the above, the present invention has been thus described in detail, but it is not fully understood why that according to the present invention it is possible to obtain a sintered zirconia article having excellent thermal shock resistance and a high sintered density. However, as a result of investigating of the physical properties of a large number of sintered articles obtained for analytical experiments of numerous factors such as various combinations of starting materials, sintering conditions, presence or absence of heat treatment, heat treatment conditions, etc., when (1) the admixture of a partially stabilized zirconia powder as a material of zirconia powder, (2) the necessity of heat treatment, (3) the ratio of cubic crystal structures in the sintered crystal structure, and (4) the diameter of the particles composing the sintered article are specified, it has been found that a sintered zirconia article can be obtained which is excellent in thermal shock resistance and has a high sintered density required for use as oxygen sensors. Therefore, the industrial value of the present invention is very great.

In the following, the present invention will be explained in further detail by way of examples, which are not intended to limit the present invention.

EXAMPLE 1

97 Parts by weight of commercially available zirconia (purity: higher than 99%, particle diameter: 1μ) and 3 parts by weight of commercially available light burned magnesia as a stabilizing agent were admixed by means of a ball mill. After the admixture was sintered at 1500° C. for one hour, the sintered admixture was pulverized by means of a vibration mill, to obtain partially stabilized zirconia powder containing 60% by weight of a cubic crystal structure and having an average particle diameter of 1.5μ.

With 20 parts by weight of the thus obtained partially stabilized zirconia powder, there were mixed 80 parts by weight of the same mixture of zirconia powder of the partially stabilized zirconia and light burned magnesia used in the preparation of the partially stabilized zirconia. Glycerin was added as a binder to this mixture, and the mixture was then shaped by a rubber press. The resulting shaped article was lathed to produce a tube having 4.5 mm in inner diameter and 7.0 mm in outer diameter with one end closed and the other end open. After this tube was sintered at 1700° C. for 10 hours, the temperature was lowered at a rate of 100° C./hour down to at 1300° C., and then the tube was heat treated at 1300° C. for 10 hours.

The physical properties of the sintered zirconia article obtained after the heat treatment were as follows:

Bulk density: 5.5 g/cm$^3$
Water absorption: 0.07%
Content of cubic phase: 44% by weight
Diameters of the particles constituting the article
  1–30μ: 15% by weight
  30–200μ: 85% by weight In order to examine the thermal shock resistance of this sintered article, the sintered tube, without being preheated, was immersed in molten iron at 1650° C. held in a high frequency furnace. After the sintered tube was held in this molten iron for 30 seconds, it was taken out and allowed to cool. The surface condition of the tube was examined, but no cracks were found.

COMPARATIVE EXAMPLE 1

Without using the partially stabilized zirconia powder of Example 1, 97 parts by weight of commercially available zirconia powder as a starting material zirconia powder and 3 parts by weight of commercially available light burned magnesia powder as a stabilizing agent were mixed, shaped, sintered and heat treated under the same conditions as in Example 1. The physical properties of the sintered zirconia article obtained after the heat treatment were as follows:

Bulk density: 5.5 g/cm$^3$
Water absorption: 0.11%
Content of cubic phase: 55% by weight
Diameters of the constituting particles: 30–200$\mu$ particles constituting approximately 100% by weight In the same way as in Example 1, this sintered article was immersed in molten iron at 1650° C. for 30 seconds and then it was allowed to cool. Upon examining the tube surface, there was observed the generation of cracks clearly detectable with the eye.

COMPARATIVE EXAMPLE 2

Without using partially stabilized zirconia powder, 97 parts by weight of commercially available coarse particle zirconia powder and 3 parts by weight of commercially available light burned magnesia were pulverized and sieved, and 20 parts by weight of particles having a particle diameter of 1–30$\mu$ and 80 parts by weight of particles having a particle diameter of 30–200$\mu$ were mixed. The mixture was then shaped, sintered and heat-treated under the same conditions as in Example 1. As regards the physical properties of the sintered zirconia article after the heat treatment, it contained a cubic phase in an amount of 55% by weight, and as for the diameters of the constituting particles, 1–30$\mu$ diameter particles constituting 20% by weight and 30–200$\mu$ diameter particles constituting 80% by weight, were used but the bulk density was 4.9 g/cm$^3$ so that the sintered density was low. Therefore the sintered article could not be put into practical use as oxygen sensors.

EXAMPLE 2

Using the conditions shown in Table 1 sintered zirconia articles were produced in the same way as in Example 1. Thermal shock resistance tests were carried out under the same conditions as in Example 1.

The results are shown in Table 1.

TABLE 1

| Run No. | Partially stabilized zirconia powder (wt. parts) | Kind of stabilizers | Zirconia powder + stabilizer (wt. parts) | Sintering condition (temp. × hours) °C. | Heat treatment condition (temp. × hours) |
|---|---|---|---|---|---|
| 1 | 30 | CaO | 70 | 1700 × 10 | Temp. drop speed to 1300° C. 100° C./hr; 1300° C. × 10 hr |
| 2 | 20 | Y$_2$O$_3$ | 80 | 1700 × 10 | Temp. drop speed to 1300° C. 100° C./hr; 1300° C. × 10 hr |
| 3 | 30 | CaO + Y$_2$O$_3$ | 70 | 1700 × 10 | Temp. drop speed to 1300° C. 100° C./hr; 1300° C. × 10 hr |
| 4 | 10 | MgO | 90 | 1650 × 10 | Temp. drop speed to 1300° C. 80° C./hr; 1300° C. × 10 hr |
| 5 | 20 | MgO | 80 | 1650 × 10 | Temp. drop speed to 1300° C. 80° C./hr; 1300° C. × 10 hr |
| 6 | 20 | MgO | 80 | 1700 × 10 | Temp. drop speed to 1300° C. 100° C./hr; 1300° C. × 10 hr |
| 7 | 40 | MgO | 60 | 1700 × 10 | Temp. drop speed to 1300° C. 100° C./hr; 1300° C. × 10 hr |
| 8 | 5 | MgO | 95 | 1700 × 10 | Temp. drop speed to 1300° C. 100° C./hr; 1300° C. × 10 hr |
| 9 | 80 | MgO | 20 | 1700 × 10 | Temp. drop speed to 1300° C. 100° C./hr; 1300° C. × 10 hr |
| 10 | 0 | MgO | 100 | 1700 × 10 | No heat treatment |
| 11 | 20 | MgO | 80 | 1700 × 10 | No heat treatment |
| 12 | 60 | MgO | 40 | 1700 × 10 | Temp. drop speed to 1300° C. 100° C./hr; 1300° C. × 10 hr |

| Run No. | Bulk density (g/cm$^3$) | Cubic phase (wt. %) | Composing particles 1–30$\mu$ (wt. %) | Composing particles 30–200$\mu$ (wt. %) | Thermal shock resistance |
|---|---|---|---|---|---|

TABLE 1-continued

| | | | | | |
|---|---|---|---|---|---|
| 1 | 5.4 | 40 | 30 | 70 | No crack |
| 2 | 5.6 | 50 | 15 | 85 | " |
| 3 | 5.5 | 45 | 20 | 80 | " |
| 4 | 5.5 | 51 | 10 | 90 | " |
| 5 | 5.5 | 46 | 20 | 80 | " |
| 6 | 5.5 | 45 | 15 | 85 | " |
| 7 | 5.4 | 32 | 35 | 65 | " |
| 8 | 5.5 | 49 | 2 | 98 | Cracks present |
| 9 | 5.1 | 11 | 70 | 30 | No cracks |
| 10 | 5.6 | 97 | 0 | 100 | Collapsed |
| 11 | 5.6 | 80 | 5 | 95 | " |
| 12 | 5.2 | 21 | 50 | 50 | Cracks present |

What is claimed is:

1. A method of producing a sintered zirconia article, comprising the steps of mixing 10–50% by weight of a partially stabilized zirconia powder obtained by adding a stabilizing agent to a zirconia powder and admixing, sintering the admixture and pulverizing the sintered admixture, and 90–50% by weight of a zirconia powder and a stabilizing agent; shaping the resulting mixture, sintering the shaped article and then heat treating the sintered article at a temperature of from 1200° to 1500° C., thereby to obtain a sintered zirconia article composed of a cubic phase crystal which has a crystalline structure of not more than 70% by weight and which is made up of 5–40% by weight of particles having a diameter range of 1–30$\mu$ and 95–60% by weight of particles having a diameter range of 30–300$\mu$.

2. A method according to claim 1 wherein the stabilizing agent is one member selected from the group consisting of CaO, MgO and $Y_2O_3$.

3. A method according to claim 1 wherein the stabilizing agent is added to the starting material zirconia powder in an amount of not more than 15 mol %.

4. A method according to claim 1 wherein the starting zirconia powder material, stabilizing agents and partially stabilized zirconia powder is made up of particles having diameters not larger than 20$\mu$.

5. A method according to claim 1 wherein the sintering takes place at a temperature of from 1500° to 1900° C. and for a period of 0.5 to 30 hours.

6. A method according to claim 1 wherein the heat treatment is carried out for a period of 1 to 30 hours.

7. A method according to claim 1 wherein the sintered article is composed of a 10–50% by weight of cubic phase crystalline structure.